(12) United States Patent
Kishore et al.

(10) Patent No.: US 7,964,737 B2
(45) Date of Patent: Jun. 21, 2011

(54) PROCESS FOR PRODUCING 2-(N-BUTYL)-3-[[2'-(TETRAZOL-5-YL)BIPHENYL-4-YL]METHYL]-1,3-DIAZASPIRO[4.4]NON-1-EN-4-ONE

(75) Inventors: Charugundla Kishore, Mysore (IN); Vinod Vishwanath Bandi, Mysore (IN); Rajappa Murali, Mysore (IN); Mysore A. Sathish, Mysore (IN); Sulur G. Manjunatha, Mysore (IN)

(73) Assignee: Jubilant Organosys Limited, Noida (IN)

( * ) Notice: Subject to any disclaimer, the term of this patent is extended or adjusted under 35 U.S.C. 154(b) by 273 days.

(21) Appl. No.: 11/997,041

(22) PCT Filed: Jul. 27, 2006

(86) PCT No.: PCT/IN2006/000266
§ 371 (c)(1),
(2), (4) Date: May 22, 2008

(87) PCT Pub. No.: WO2007/013101
PCT Pub. Date: Feb. 1, 2007

(65) Prior Publication Data
US 2008/0214830 A1    Sep. 4, 2008

(30) Foreign Application Priority Data

Jul. 27, 2005 (IN) .......................... 1988/DEL/2005
Dec. 30, 2005 (IN) .......................... 3541/DEL/2005

(51) Int. Cl.
C07D 257/04    (2006.01)
(52) U.S. Cl. ..................................................... 548/253
(58) Field of Classification Search ............... 548/253, 548/300.7
See application file for complete search history.

(56) References Cited

FOREIGN PATENT DOCUMENTS

| EP | 0 708 103 | 4/1996 |
| WO | 99 38847 | 8/1999 |
| WO | 2004 007482 | 1/2004 |
| WO | 2005 051943 | 6/2005 |

OTHER PUBLICATIONS

IN 193265 (Accession No. 146:379983) retrieved from CAPLUS on May 2010.*

* cited by examiner

Primary Examiner — Shawquia Young
(74) Attorney, Agent, or Firm — Oblon, Spivak, McClelland, Maier & Neustadt, L.L.P.

(57) ABSTRACT

Disclosed herein a process for producing 2-(n-butyl)-3-[[2'-(tetrazol-5-yl)biphenyl-4-yl]methyl]-1,3-diazaspiro[4.4] non-1-en-4-one of formula (I) in pure form by using selective solvent system and cost efficient raw materials and reagents.

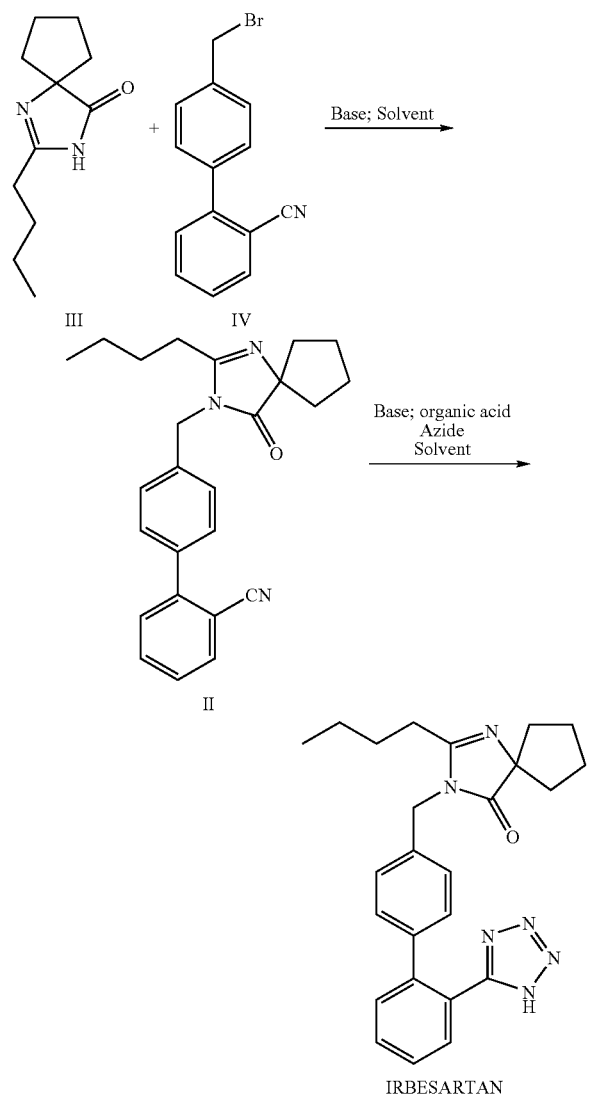

18 Claims, No Drawings

PROCESS FOR PRODUCING 2-(N-BUTYL)-3-[[2'-(TETRAZOL-5-YL)BIPHENYL-4-YL]METHYL]-1,3-DIAZASPIRO[4.4]NON-1-EN-4-ONE

FIELD OF THE INVENTION

This invention, in general, relates to a process for producing 2-(n-butyl)-3-[[2'-(tetrazol-5-yl)biphenyl-4-yl]methyl]-1,3-diazaspiro[4.4]non-1-en-4-one (Irbesartan). In particular the present invention provides a novel process for producing 2-(n-butyl)-3-[[2'-(tetrazol-5-yl)biphenyl-4-yl]methyl]-1,3-diazaspiro[4.4]non-1-en-4-one in pure form by using selective solvent system and cost efficient raw materials.

BACKGROUND OF THE INVENTION 2-(n-butyl)-3-[[2'-(tetrazol-5-yl)biphenyl-4-yl]methyl]-1,3-diazaspiro[4.4]non-1-en-4-one (Irbesartan) is represented by Formula I.

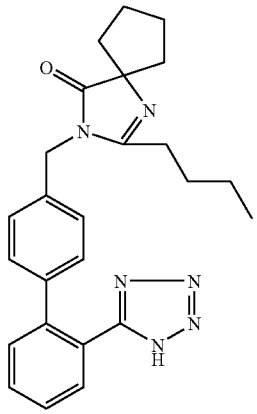

I

Irbesartan is a powerful angiotensin II receptor antagonist (blocker). Angiotensin is an important participant in the renin-angiotensin-aldosterone system (RAAS) and has a strong influence on blood pressure.

Many processes are disclosed in the art for the preparation of Irbesartan. Irbesartan has been generally prepared as per the process disclosed in EP-A-0 454 511, i.e. by reaction of 2-(n-butyl)-3-[[2'-(cyano)biphenyl-4-yl]methyl]-1,3-diazaspiro[4.4]non-1-en-4-one either with tributyltin azide and triphenyl chloromethane in xylene at reflux, by elimination of the triphenylmethyl protecting group and by isolation from a solution in ethyl acetate, duly dried. The other commonly used process is disclosed in C. A. Bernhart et al., J. Med. Chem., 1993, 36, 3371-3380. The process involves reaction of 2-(n-butyl)-3-[[2'-(cyano)biphenyl-4-yl]methyl]-1,3-diazaspiro[4.4]non-1-en-4-one directly with tributyltin azide, in xylene at reflux and isolation from a solution in dichloromethane, duly dried. The compound thus prepared, [Formula (I)], is presented in the form of stable, non-hygroscopic needles, which can be stored and formulated without any degradation.

U.S. Pat. Nos. 5,196,444 and 5,399,578 and describe similar procedures for the synthesis of some non-peptide angiotensin II inhibitors wherein the use of trimethyltin azide is reported in presence of toluene as a solvent for the conversion of aromatic nitrles into tetrazoles. All these processes require trialkyltin azide as a reagent, which is not safe to handle and is costly. The reaction time is usually long, ranging from 36 hours to 4 days. The isolation of product from such reaction mixtures can be tedious, requiring several critical layer separations, and the yield obtained is generally low.

U.S. Pat. No. 5,629,331 describes a process for the preparation of Irbesartan Form A and B wherein the aromatic nitrile is treated with sodium azide in presence of triethylamine hydrochloride in 1-methylpyrrolidin-2-one as solvent at a temperature of 121-123° C. The solvent used is costly and not easily recovered, making the process unsuitable for commercial scale production.

U.S. Pat. No. 6,162,922 has described a process for the preparation of Irbesartan which involves treating the Spiro intermediate of Formula III with halomethyl cyanobiphenyl intermediate of Formula IV in presence of a water and water immiscible solvent, a base and a phase transfer catalyst.

The processes known in the prior art for preparing Irbesartan involve tedious workup procedures, e.g., a large number of steps, which include the protection and subsequent deprotection, and isolation of intermediates, as well as separations by column chromatography. The processes of the art involve tedious workup to isolate the required product and this results in excessive production times, which in turn renders the process more costly and less eco-friendly; thus the processes are not suitable for commercial scale up. Accordingly, there remains a need for a simple, commercially advantageous process.

SUMMARY OF THE INVENTION

It is a principal object of the present invention to provide an industrially viable process for producing 2-(n-butyl)-3-[[2'-(tetrazol-5-yl)biphenyl-4-yl]methyl]-1,3-diazaspiro[4.4]non-1-en-4-one of Formula I employing selective solvent system and cost efficient raw materials.

Another object of the present invention is to provide an industrially viable process for producing 2-(n-butyl)-3-[['-(tetrazol-1-yl)biphenyl-4-yl]methyl]-1,3-diazaspiro[4.4]non-1-en-4-one of Formula I, wherein the solvents used in the process are recoverable and reusable.

Further object of the present invention is to provide an industrially viable process for producing 2-(n-butyl)-3-[[2'-(tetrazol-5-yl)biphenyl-4-yl]methyl]-1,3-diazaspiro[4.4]non-1-en-4-one of Formula I, wherein the process employs condensation reaction using selective solvent system in presence of a base to prepare an intermediate 2-(n-butyl)-3-[[2'-(cyano)biphenyl-4-yl]methyl]-1,3-diazaspiro[4.4]non-1-en-4-one of Formula II with good yield and purity to produce said compound of Formula I.

Yet another object of the present invention is to provide an industrially viable process for producing 2-(n-butyl)-3-[[2'-(tetrazol-5-yl)biphenyl-4-yl]methyl]-1,3-diazaspiro[4.4]non-1-en-4-one of Formula I, wherein said intermediate of Formula II is optionally purified employing selective solvent, avoiding the use of column chromatographic purification.

Yet another object of the present invention is to provide an industrially viable process for producing 2-(n-butyl)-3-[[2'-(tetrazol-5-yl)biphenyl-4-yl]methyl]-1,3-diazaspiro[4.4]non-1-en-4-one of Formula I, wherein said compound of Formula I is obtained by simple crystallization employing a selective solvent to avoid multiple purification steps.

The above and other objects are attained in accordance with the present invention wherein there is provided following embodiments, however the described embodiments hereinafter is in accordance with the best mode of practice and the invention is not restricted to the particular embodiments.

In accordance with one preferred embodiment of the present invention, there is provided a process for producing 2-(n-butyl)-3-[[2'-(tetrazol-5-yl)biphenyl-4-yl]methyl]-1,3-diazaspiro[4.4]non-1-en-4-one of Formula I comprising condensing 2-(n-butyl)-1,3-diazaspiro[4,4]non-1-ene-4-one of Formula III or acid addition salt thereof with 4-(bromomethyl)-2'-cyanobiphenyl of Formula IV in the presence of base and mixture of solvents to get an intermediate 2-(n-butyl)-3-[[2'-(cyano)biphenyl-4-yl]methyl]-1,3-diazaspiro[4.4]non-1-en-4-one of Formula II, treating the intermediate of Formula II with azide in the presence of organic base and organic acid and optionally employing a solvent, and isolating the final product 2-(n-butyl)-3-[[2'-(tetrazol-5-yl)biphenyl-4-yl]methyl]-1,3-diazaspiro[4.4]non-1-en-4-one of Formula I.

In accordance with one preferred embodiment of the present invention, there is provided a process for producing 2-(n-butyl)-3-[[2'-(tetrazol-5-yl)biphenyl-4-yl]methyl]-1,3-diazaspiro[4.4]non-1-en-4-one of formula I, comprising condensing 2-(n-butyl)-1,3-diazaspiro[4,4]non-1-ene-4-one of Formula III or acid addition salt thereof with 4-(bromomethyl)-2'-cyanobiphenyl of Formula IV in the presence of base and mixture of polar aprotic solvent and non polar solvents to get an intermediate 2-(n-butyl)-3-[[2'-(cyano)biphenyl-4-yl]methyl]-1,3-diazaspiro[4.4]non-1-en-4-one of Formula II, wherein said mixture of solvents used herein are selected from the group comprising any organic solvent preferably toluene, xylene, dimethylformamide or dimethyl sulfoxide.

In accordance with one preferred embodiment of the present invention, there is provided a process for producing 2-(n-butyl)-3-[[2'-(tetrazol-5-yl)biphenyl-4-yl]methyl]-1,3-diazaspiro[4.4]non-1-en-4-one of Formula I, comprising condensing 2-(n-butyl)-1,3-diazaspiro[4,4]non-1-ene-4-one of Formula III or acid addition salt thereof with 4-(bromomethyl)-2'-cyanobiphenyl of Formula IV in the presence of base and a mixture of solvents selected from polar aprotic solvent and non polar solvents to get an intermediate 2-(n-butyl)-3-[[2'-(cyano)biphenyl-4-yl]methyl]-1,3-diazaspiro[4.4]non-1-en-4-one of Formula II, wherein said mixture of solvents used is preferably a mixture of dimethylformamide and toluene.

In accordance with another embodiment of the present invention, the intermediate 2-(n-butyl)-3-[[2'-(cyano)biphenyl-4-yl]methyl]-1,3-diazaspiro[4.4]non-1-en-4-one of Formula II, is optionally purified in presence of mixture of water and an alcoholic solvent.

In accordance with yet another preferred embodiment of the present invention, there is provided a process for producing 2-(n-butyl)-3-[[2'-(tetrazol-5-yl)biphenyl-4-yl]methyl]-1,3-diazaspiro[4.4]non-1-en-4-one of Formula I, wherein the intermediate 2-(n-butyl)-3-[[2'-(cyano)biphenyl-4-yl]methyl]-1,3-diazaspiro[4.4]non-1-en-4-one of Formula II is further treated with azide in the presence of organic base and organic acid and optionally employing a solvent to obtain 2-(n-butyl)-3-[[2'-(tetrazol-5-yl)biphenyl-4-yl]methyl]-1,3-diazaspiro[4.4]non-1-en-4-one of Formula I.

In accordance with yet another preferred embodiment of the present invention, there is provided a process for producing 2-(n-butyl)-3-[[2'-(tetrazol-5-yl)biphenyl-4-yl]methyl]-1,3-diazaspiro[4.4]non-1-en-4-one of Formula I, wherein the intermediate 2-(n-butyl)-3-[[2'-(cyano)biphenyl-4-yl]methyl]-1,3-diazaspiro[4.4]non-1-en-4-one of Formula II is further treated with azide in the presence of organic base and organic acid and optionally employing a solvent, wherein said solvent is selected from aromatic or aliphatic hydrocarbons, ethers, ketones, esters or alcohols or mixtures thereof.

DESCRIPTION OF THE INVENTION

The present invention provides a novel, economical and a high yielding process for the industrial production of 2-(n-butyl)-3-[[2'-(tetrazol-5-yl)biphenyl-4-yl]methyl]-1,3-diazaspiro[4.4]non-1-en-4-one of Formula I employing readily available raw materials and reagents.

The process disclosed according to the present invention does not involve any chromatographic purification method for intermediates or final product. Also, the use of organotin reagent for the formation of tetrazole from cyano as a starting material, as disclosed in prior art, is avoided. Further, the process is carried out in the presence of a solvent i.e. hydrocarbon which is easily recovered and recycled, thereby providing the 2-(n-butyl)-3-[[2'-(tetrazol-5-yl)biphenyl-4-yl]methyl]-1,3-diazaspiro[4.4]non-1-en-4-one of Formula I with high quality without using multiple purification steps.

The process for producing 2-(n-butyl)-3-[[2'-(tetrazol-5-yl)biphenyl-4-yl]methyl]-1,3-diazaspiro[4.4]non-1-en-4-one of Formula I (Irbesartan) is described in scheme 1.

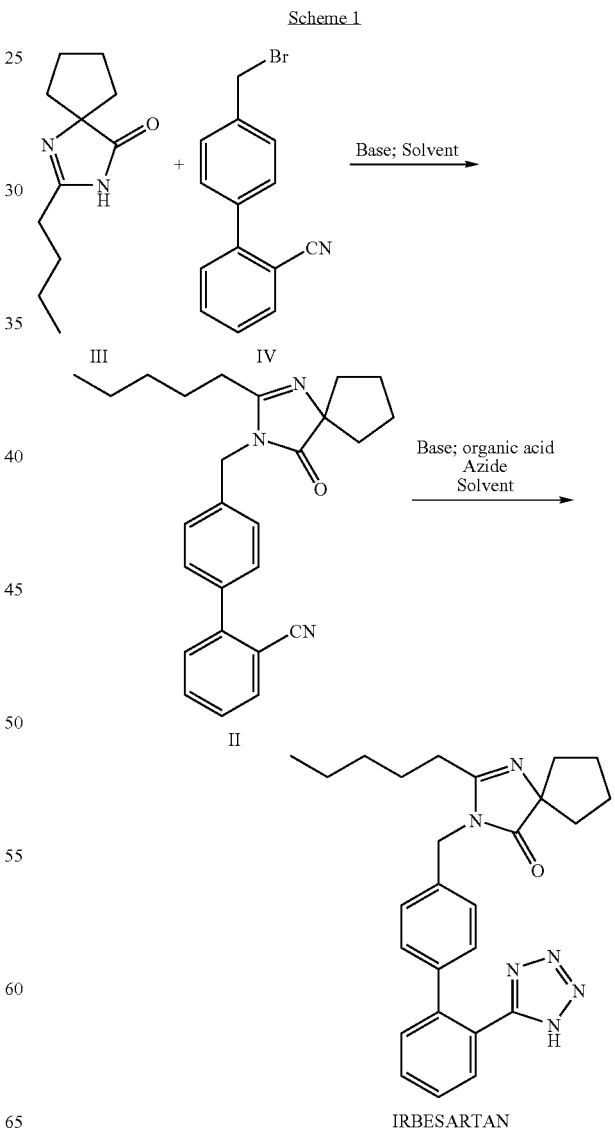

Scheme 1

The process involves condensation of 2-(n-butyl)-1,3-diazaspiro[4,4]non-1-ene-4-one of Formula III or its acid addition salt with 4-(bromomethyl)-2'-cyanobiphenyl of Formula IV in the presence of base and a mixture of polar aprotic solvent and a non-polar solvent, wherein said acid addition salt of Formula III is selected from the group consisting of, but not limited to, hydrochloride, hydro bromide, hydrogen sulfate, preferably hydrochloride. The base used herein is selected from the group consisting of, but not limited to, alkoxide of alkali metal such as sodium methoxide, potassium methoxide, sodium tert-butoxide, potassium tert-butoxide; hydrides of alkali metal such as sodium hydride; hydroxide of alkali metal such as sodium hydroxide, potassium hydroxide, cesium hydroxide; carbonates of alkali metal such as cesium carbonate, potassium carbonate or sodium, carbonate. The preferred base used herein is hydroxide of alkali metal such as sodium hydroxide, potassium hydroxide, cesium hydroxide and more preferably sodium hydroxide.

According to the present invention, said condensation reaction is carried out in a mixture of solvents in the presence of base, and it is found that the formation of impurities is very less as compared to the condensation reaction carried out in a single solvent. The solvents used herein are selected from the group comprising of polar aprotic solvent and a non-polar solvent preferably toluene, xylene, tetrahydrofuran, dimethylformamide or dimethyl sulfoxide, more preferably mixture of dimethylformamide and toluene.

The condensation reaction is carried out at a temperature in the range of about 0-60° C., preferably at a temperature in the range of about 25° C.-40° C. After the completion of the reaction, reaction mass is diluted with water and aqueous layer is separated from the organic layer and extracted with organic solvent. The combined organic layer is washed with water, dried and concentrated under reduced pressure to get residue. The residue can be taken further for reaction with azide or preferably purified from a mixture of water and an alcoholic solvent to get a compound of Formula II as a solid material with improved yield and high purity. The organic solvent used herein selected from the group comprising toluene or xylene, preferably toluene and wherein said alcoholic solvent is selected from methanol, ethanol or isopropyl alcohol.

The compound of Formula II is reacted with azide in the presence of organic base and organic acid and optionally employing a solvent to get compound of Formula I. The azide used herein is alkali metal azide, preferably sodium azide. The organic base used is triethyl amine. The organic acid used herein is selected from $C_1$-$C_4$ carboxylic acid, preferably acetic acid.

The solvent used herein is selected from the group comprising aromatic or aliphatic hydrocarbons such as heptane, toluene or xylene, ketones such as methyl isobutyl ketone, esters such as n-butyl acetate, ethers such as dioxane or alcohols such as n-butanol.

The reaction is carried out at a temperature in the range of about 70° C. to 140° C., preferably in the range of about 115° C. to about 130° C. According to the present invention, sodium azide and organic base/organic acid are used in proportions of 1:1 to 1:6 moles per mole of starting nitrile, preferably 1:2 to 1:4 moles per mole of starting nitrile, more preferably 1:2 mole per mole of starting nitrile. Upon 10-25 hours of heating, the reaction is over and the reaction mixture is treated according to the conventional techniques, more particularly, the mixture is basified by the addition of base preferably alkaline hydroxide, in aqueous solution. The mixture then separate into three layers namely, upper organic layer, middle product layer and lower aqueous layer. The aqueous phase containing the salts, particularly chlorides and azides is removed and the oily phase is treated with water and organic solvent, such as xylene, to eliminate the reaction byproducts. The resultant aqueous phase, containing the alkaline salt of the 2-(n-butyl)-3-[[2'-(tetrazol-5-yl)biphenyl-4-yl]methyl]-1,3-diazaspiro[4.4]non-1-en-4-one is subjected to acidification, preferably by addition of aqueous hydrochloric acid until the pH is between 2.0 and 4.0, preferably between 2.5 and 3.0 to obtain the crude 2-(n-butyl)-3-[[2'-(tetrazol-5-yl)biphenyl-4-yl]methyl]-1,3-diazaspiro[4.4]non-1-en-4-one, which is further washed with water and ethyl acetate.

The crude material is recrystallized in from an alcoholic solvent to get Irbesartan in highly pure form.

The following non-limiting examples illustrate specific embodiments of the present invention. They are, however, not intended to be limiting the scope of the present invention in any way.

Example 1

Preparation of 2-(n-butyl)-3-[[2'-(cyano)biphenyl-4-yl]methyl]-1,3-diazaspiro[4.4]non-1-ene-4-one (II)

A RB flask was charged with 2-(n-butyl)-1,3-diazaspiro[4,4]non-1-ene-4-one (7.0 g), toluene (70 ml), DMF (30 ml) and sodium methoxide (2.2 g) at room temperature and stirred for 15 min, followed by the addition of 4-(bromomethyl)-2'-cyanobiphenyl (10 g). The reaction mixture was stirred for 1 hour and then quenched by the addition of water (100 ml). The layers were separated and organic layer was evaporated to get oily residue. The obtained residue was taken in isopropyl alcohol (10 ml) and water (10 ml) and stirred at room temperature to get solid material. The solid material was filtered and washed with IPA and water mixture and then dried under vacuum.

Example 2

A RB flask was charged with 2-(n-butyl)-1,3-diazaspiro[4,4]non-1-ene-4-one (7.0 g), toluene (70 ml) and DMF (30 ml). 4-(Bromomethyl)-2'-cyanobiphenyl (10 g) and sodium hydroxide (1.6 g) was added to reaction mixture and stirred at room temperature. The reaction was quenched by the addition of water (100 ml). Then the layers were separated and organic layer was evaporated to get oily residue, which was taken in isopropyl alcohol (10 ml) and water (10 ml) and stirred at room temperature to get solid material. The solid material was filtered and washed with IPA and water mixture and then dried under vacuum.

Example 3

A RB flask was charged with 2-(n-butyl)-1,3-diazaspiro[4,4]non-1-ene-4-one (7.0 g), toluene (70 ml) and DMF (30 ml), followed by the addition of 4-(Bromomethyl)-2'-cyanobiphenyl (10 g). The reaction mixture was cooled to 10-15° C. and then cesium carbonate (13.0 g) was added to it. The reaction mixture was stirred at room temperature for 1 hour and then the reaction was quenched by addition of water (100 ml). The layers were separated and organic layer was evaporated to get oily residue, which was taken in isopropyl alcohol (10 ml) and water (10 ml) and stirred at room temperature to get solid material. The solid material was filtered and washed with IPA and water mixture and then dried under vacuum.

Example 4

A RB flask was charged with 2-(n-butyl)-1,3-diazaspiro[4,4]non-1-ene-4-one (7.0 g), toluene (70 ml) and DMF (30 ml), followed by the addition of 4-(Bromomethyl)-2'-cyanobiphenyl (10 g). The reaction mixture was cooled to 10-15° C. and then potassium carbonate (5.0 g) was added to it. The reaction mixture was stirred at room temperature for 1 hour and then the reaction was quenched by addition of water (100 ml). The layers were separated and organic layer was evaporated to get oily residue, which was taken in isopropyl alcohol (10 ml) and water (10 ml) and stirred at room temperature to get solid material. The solid material was filtered and washed with IPA and water mixture and then dried under vacuum.

Example 5

A RB flask was charged with 2-(n-butyl)-1,3-diazaspiro[4,4]non-1-ene-4-one (7.0 g), toluene (70 ml) and DMF (30 ml), followed by the addition of 4-(Bromomethyl)-2'-cyanobiphenyl (10 g). The reaction mixture was cooled to 10-15° C. and then potassium tert-butoxide (4.6 g) was added to it. The reaction mixture was stirred at room temperature for 1 hour and then the reaction was quenched by addition of water (100 ml). The layers were separated and organic layer was evaporated to get oily residue. The obtained residue was taken in isopropyl alcohol (10 ml) and water (10 ml) and stirred at room temperature to get solid material, which was filtered and washed with IPA and water mixture and then dried under vacuum.

Example 6

Preparation of 2-(n-butyl)-3-[[2'-(tetrazol-5-yl)biphenyl-4-yl]methyl]-1,3-diazaspiro[4.4]non-1-en-4-one
(I)

A RB flask was charged with n-butyl Acetate (50 ml), triethyl amine (22 ml) and acetic acid (9 ml) and stirred. 2-(n-butyl)-3-[[2'-(cyano)biphenyl-4-yl]methyl]-1,3-diazaspiro[4.4]non-1-en-4-one (10 g) and sodium Azide (3.4 g) was added to the flask and the reaction mixture was heated at 115-120° C. for 24 hrs, followed by cooling. The reaction was then quenched by addition of water (30 ml). The pH of the aqueous layer was adjusted between 10 to 11 with 30% Sodium hydroxide and then stirred for 10 min. Layers were separated and oily layer was treated with water and xylene. The pH of the aqueous layer was adjusted between 2 and 3 by the addition of hydrochloric acid and then stirred for 1 hour, filtered to obtain solid material which was washed with water (20 ml) and ethyl Acetate (5 ml) and dried at 90-100° C.

Example 7

A RB flask was charged with n-heptane (50 ml), triethyl amine (22 ml) and acetic acid (9 ml) and stirred. 2-(n-butyl)-3-[[2'-(cyano)biphenyl-4-yl]methyl]-1,3-diazaspiro[4.4]non-1-en-4-one (10 g) and sodium azide (3.4 g) was added to the flask and the reaction mixture was heated at 100-105° C. for 24 hrs, followed by cooling. The reaction was then quenched by addition of water (30 ml). The pH of the aqueous layer was adjusted between 10 to 11 with 30% Sodium hydroxide and then stirred for 10 min. Layers were separated and pH of the aqueous layer was adjusted between 2 and 3 by the addition of hydrochloric acid and stirred for 1 hour, filtered to obtain solid material which was washed with water (20 ml) and ethyl acetate (5 ml) and then dried at 90-100° C.

Example 8

A RB flask was charged with toluene (50 ml), triethyl amine (22 ml) and acetic acid (9 ml) and stirred. 2-(n-butyl)-3-[[2'-(cyano)biphenyl-4-yl]methyl]-1,3-diazaspiro[4.4]non-1-en-4-one (10 g) and sodium azide (3.4 g) was added to the flask and the reaction mixture was heated at 1115-120° C. for 24 hrs, followed by cooling. The reaction was then quenched by the addition of water (30 ml). The pH of the aqueous layer was adjusted between 10 to 11 with 30% Sodium hydroxide and stirred for 10 min. Layers were separated and oily layer was treated with water and xylene. The pH of the aqueous layer was adjusted between 2 and 3 by the addition of hydrochloric acid and stirred for 1 hour, filtered to obtain solid material which was washed with water (20 ml) and ethyl acetate (5 ml) and then dried at 90-100° C.

Example 9

A RB flask was charged with n-butanol (50 ml), triethyl amine (22 ml) and acetic acid (9 ml) and stirred. 2-(n-butyl)-3-[[2'-(cyano)biphenyl-4-yl]methyl]-1,3-diazaspiro[4.4]non-1-en-4-one (10 g) and sodium azide (3.4 g) was added to the flask and the reaction mixture was heated at 115-120° C. for 24 hrs, followed by cooling. The reaction was then quenched by the addition of water (30 ml). The pH of the aqueous layer was adjusted between 10 to 11 with 30% Sodium hydroxide and stirred for 10 min. Layers were separated and oily layer was treated with water and xylene. The pH of the aqueous layer was adjusted between 2 and 3 by the addition of hydrochloric acid and stirred for 1 hour, filtered to obtain solid material which was washed with water (20 ml) and ethyl acetate (5 ml) and then dried at 90-100° C.

Example 10

A RB flask was charged with methyl isobutyl ketone (50 ml), triethyl amine (22 ml) and acetic acid (9 ml) and stirred. 2-(n-butyl)-3-[[2'-(cyano)biphenyl-4-yl]methyl]-1,3-diazaspiro[4.4]non-1-en-4-one (10 g) and sodium azide (3.4 g) was added to the flask and the reaction mixture was heated at 115-120° C. for 24 hrs, followed by cooling. The reaction was then quenched by the addition of water (30 ml). The pH of the aqueous layer was adjusted between 10 to 11 with 30% Sodium hydroxide and stirred for 10 min. Layers were separated and oily layer was treated with water and xylene. The pH of the aqueous layer was adjusted between 2 and 3 by the addition of hydrochloric acid and stirred for 1 hour, filtered to obtain solid material which was washed with water (20 ml) and ethyl acetate (5 ml) and then dried at 90-100° C.

Example 11

A RB flask was charged with xylene (50 ml), triethyl amine (15 ml) and acetic acid (6 ml) and stirred. 2-(n-butyl)-3-[[2'-(cyano)biphenyl-4-yl]methyl]-1,3-diazaspiro[4.4]non-1-en-4-one (10 g) and sodium azide (3.4 g) was added to the flask and the reaction mixture was heated at 120-125° C. for 24 hrs, followed by cooling. The reaction was then quenched by the addition of water (30 ml). The pH of the aqueous layer was adjusted between 10 to 11 with 30% Sodium hydroxide and stirred for 10 min. Layers were separated and oily layer was treated with water and xylene. The pH of the aqueous layer was adjusted between 2 and 3 by the addition of hydrochloric acid and stirred for 1 hour, filtered to obtain solid material which was then washed with water (20 ml) and ethyl acetate (5 ml) and then dried at 90-100° C.

Example 12

A RB flask was charged with triethyl amine 22 ml and acetic acid 9 ml and stirred. 2-(n-butyl)-3-[[2'-(cyano)biphenyl-4-yl]methyl]-1,3-diazaspiro[4.4]non-1-en-4-one (10 g) and sodium azide (3.4 g) was added to the flask and the reaction mixture was heated at 90-100° C. for 24 hrs, followed by cooling. The reaction was then quenched by the addition of water (30 ml) and xylene (30 ml). The pH of the aqueous layer was adjusted between 10 to 11 with 30% Sodium hydroxide and stirred for 10 min, Layers were separated and oily layer was treated with water and xylene. The pH of the aqueous layer was adjusted between 2 and 3 by the addition of hydrochloric acid and stirred for 1 hour, filtered to obtain solid material which was then washed with water (20 ml) and ethyl acetate (5 ml) and then dried at 90-100° C.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. A process for producing purified 2-(n-butyl)-3[[2'-(tetrazol-5-yl)biphenyl-4-yl]methyl]-1,3-diazaspiro[4.4]non-1-en-4-one, comprising:
   (a) condensing 2-(n-butyl)-1,3-diazaspiro[4.4]non-1-ene-4-one or an acid addition salt thereof with 4-(bromomethyl)-2'-cyanobiphenyl of in the presence of a base, wherein the base comprises at least one alkoxide, hydride, hydroxide or carbonate of an alkali metal, and a mixture of solvents comprising at least one polar aprotic solvent and at least one non-polar solvent, wherein the solvents in the mixture of solvents are selected from the groups consisting of polar aprotic and non-polar solvents, to produce 2-(n-butyl)-3[[2'-(cyano)biphenyl-4-yl]methyl]-1,3-diazaspiro[4.4]non-1-en-4-one, which is purified in presence of mixture of water and an alcoholic solvent;
   (b) treating the purified 2-(n-butyl)-3[[2'-(cyano)biphenyl-4-yl]methyl]-1,3-diazaspiro[4.4]non-1-en-4-one with azide in the presence of an triethyl amine and acetic acid employing a solvent medium, wherein the solvent medium comprises at least one solvent selected from the group consisting of aliphatic hydrocarbons, ketones, esters, ethers, alcohols, toluene and xylene, to produce 2-(n-butyl)-3-[[2'-(tetrazol-5-yl)biphenyl-4-yl]methyl]-1,3-diazaspiro[4.4]non-1-en-4-one; and
   (c) isolating the 2-(n-butyl)-3-[[2'-(tetrazol-5-yl)biphenyl-4-yl]methyl]-1,3-diazaspiro[4.4]non-1-en-4-one employing an organic solvent, to obtain the purified 2-(n-butyl)-3-[[2'-(tetrazol-5-yl)biphenyl-4-yl]methyl]-1,3-diazaspiro[4.4]non-1-en-4-one.

2. The process according to claim 1, wherein the acid addition salt is a hydrochloride, hydro bromide or hydrogen sulfate of the 2-(n-butyl)-1,3-diazaspiro[4,4]non-1-ene-4-one.

3. The process according to claim 1, wherein the base comprises sodium methoxide, potassium methoxide, sodium tert-butoxide, potassium tert-butoxide, sodium hydride, sodium hydroxide, potassium hydroxide, cesium hydroxide, cesium carbonate, potassium carbonate or sodium carbonate.

4. The process according to claim 3, wherein the base comprises sodium hydroxide or potassium hydroxide.

5. The process according to claim 1, wherein the solvents in the mixture of solvents are selected from the group consisting of toluene, xylene, dimethylformamide, dimethyl sulfoxide and mixtures thereof.

6. The process according to claim 1, wherein the mixture of solvents comprises toluene and dimethylformamide.

7. The process according to claim 1, wherein the alcoholic solvent comprises methanol, ethanol or isopropyl alcohol.

8. The process according to claim 1, wherein the solvent medium is selected from the group consisting of n-heptane, methyl isobutyl ketone, n-butyl acetate, dioxane, n-butanol and mixtures thereof.

9. The process according to claim 1, wherein the organic solvent is selected from the group consisting of methanol, ethanol, isopropyl alcohol and mixtures thereof.

10. The process according to claim 1, further comprising treating the 2-(n-butyl)-3-[[2'-(cyano)biphenyl-4-yl]methyl]-1,3-diazaspiro[4.4]non-1-en-4-one with an azide in the presence of an organic base and an organic acid and optionally employing a solvent medium to obtain 2-(n-butyl)-3-[[2'-(tetrazol-5-yl)biphenyl-4-yl]methyl]-1,3-diazaspiro[4.4]non-1-en-4-one.

11. The process according to claim 1, wherein the solvent medium comprises at least one member selected from the group consisting of aliphatic hydrocarbons, ketones, esters, ethers and alcohols.

12. The process according to claim 1, wherein the solvent medium is comprises at least one member selected from the group consisting of n-heptane, toluene, xylene, methyl isobutyl ketone, n-butyl acetate, dioxane and n-butanol.

13. The process according to claim 8, wherein the solvent is recoverable and reusable in the process.

14. The process according to claim 1, wherein condensation (a) is conducted at a temperature of 0-60° C.

15. The process according to claim 1, wherein condensation (a) is conducted at a temperature of 25-40° C.

16. The process according to claim 1, wherein treatment (b) is conducted at a temperature of 70-140° C.

17. The process according to claim 1, wherein treatment (b) is conducted at a temperature of 115-130° C.

18. The process according to claim 1, wherein (c) comprises recrystallizing the 2-(n-butyl)-3-[[2'-(tetrazol-5-yl)biphenyl-4-yl]methyl]-1,3-diazaspiro[4,4]non-1-en-4-one in an alcoholic solvent.

* * * * *